United States Patent [19]

Bosies et al.

[11] Patent Number: 5,543,402
[45] Date of Patent: Aug. 6, 1996

[54] [3-($C_{16}$-$C_{18}$)-ALKANESULPHINYL AND SULPHONYL-2-METHOXY-METHYLPROPYL]-(2-TRIMETHYLAMMONIOETHYL) PHOSPHATES, PROCESSES FOR THE PREPARATION THEREOF AND PHARMACEUTICAL COMPOSITIONS CONTAINING THEM

[75] Inventors: Elmar Bosies, Weinheim; Dieter Herrmann, Heidelberg; Wulf Pahlke, Bensheim, all of Germany

[73] Assignee: Boehringer Mannheim GmbH, Mannheim, Germany

[21] Appl. No.: 95,478

[22] Filed: Jul. 23, 1993

Related U.S. Application Data

[63] Continuation of Ser. No. 925,407, Aug. 10, 1992, abandoned, which is a continuation of Ser. No. 758,518, Sep. 6, 1991, abandoned, which is a continuation of Ser. No. 486,658, Mar. 1, 1990, abandoned.

[30]   Foreign Application Priority Data

Mar. 4, 1989  [DE]  Germany ............... 39 06 952.4

[51] Int. Cl.⁶ .............................. A61K 31/66; C07F 9/10
[52] U.S. Cl. ..................... 514/114; 514/78; 558/169; 558/177; 554/81
[58] Field of Search ..................... 558/169; 554/78; 514/114

[56]   References Cited

U.S. PATENT DOCUMENTS

| 4,372,949 | 2/1983 | Kodama et al. | 558/169 |
| 4,444,766 | 4/1984 | Bosies et al. | 558/169 |
| 4,492,659 | 1/1985 | Bosies et al. | 558/169 |

FOREIGN PATENT DOCUMENTS

| A1-2619715 | 11/1977 | Germany | 554/78 |
| A1-2619686 | 11/1977 | Germany | 554/78 |
| C3-2009341 | 9/1979  | Germany | 554/78 |
| A1-3304870 | 8/1984  | Germany | 554/78 |

OTHER PUBLICATIONS

Vogler et al., Lipids, vol. 26 No. 12 (1991) (Presented in Tokyo, Japan in May 1989 at 3rd Intern Conf. on Lipids.

The Merck Manual, 15th Ed. (Rahway, N.J., 1987 Merck and Co.) pp. 1206–1209.

*Primary Examiner*—Mukund J. Shah
*Assistant Examiner*—Pavanaram K. Sripada
*Attorney, Agent, or Firm*—Nikaido, Marmelstein, Murray & Oram LLP

[57]   ABSTRACT

The present invention provides [3-($C_{16}$–$C_{18}$)-alkaesulphinyl- and -sulphonyl-2-methoxy-methylpropyl]-(2-trimethylammonioethyl) phosphates having superior anti-tumor activity.

12 Claims, 2 Drawing Sheets

[3-($C_{16}$-$C_{18}$)-ALKANESULPHINYL AND SULPHONYL-2-METHOXY-METHYLPROPYL]-(2-TRIMETHYLAMMONIOETHYL) PHOSPHATES, PROCESSES FOR THE PREPARATION THEREOF AND PHARMACEUTICAL COMPOSITIONS CONTAINING THEM

This application is a continuation of application Ser. No. 07/925,407 filed Aug. 10, 1992, now abandoned, which is a continuation of application Ser. No. 07/758,518 filed Sep. 6, 1991, now abandoned, which is a continuation of application Ser. No. 07/486,658 filed Mar. 1, 1990, now abandoned.

BACKGROUND OF THE INVENTION

The present invention is concerned with [3-($C_{16}$-$C_{18}$)-alkanesulphinyl- and -sulphonyl-2-methoxymethylpropyl]-(2-trimethylammonioethyl) phosphates, with the pharmacologically acceptable salts thereof, with processes for the preparation thereof, as well as with pharmaceutical compositions which contain these compounds.

Propyl-(trialkylaminoalkyl) phosphates which are substituted in the 3-position by alkylthio, alkyl-sulphinyl and alkylsulphonyl radicals are the subject of U.S. Pat. No. 4,444,766. There are described especially compounds which carry an alkyl-thio radical in the 3-position, for example (3-hexadecylthio-2-methoxymethylpropyl)-(2 -trimethylammonio-ethyl) phosphate (ilmofosine), which possesses outstanding anti-tumoral properties.

BRIEF SUMMARY OF THE INVENTION

We have now found that the analogous sulphinyl and sulphonyl compounds, as well as the corresponding heptadecyl and octadecyl derivatives, which are not described in U.S. Pat. No. 4,444,766, surprisingly show in vivo a still better action than ilmofosine, especially the two compounds (3-hexadecane-sulphonyl-2-methoxymethylpropyl)-(2 -trimethylammonio-ethyl) phosphate and (3-octadecanesulphonyl-2-methoxy-methylpropyl)-(2-trimethylammonioethyl) phosphate.

Thus, according to the present invention, there are provided compounds of the general formula:

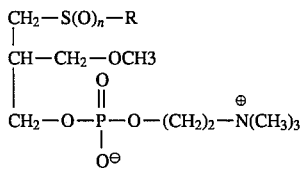

in which n is 1 or 2 and R is a straight-chained, saturated alkyl radical or group containing 16 to 18 carbon atoms, the stereoisomers thereof, as well as the pharmacologically acceptable salts thereof.

Compounds of general formula I are preferred in which n is 1 or 2 and R is a hexadecyl or octadecyl radical.

Especially preferred are 3-(hexadecanesulphonyl-2-methoxymethylpropyl)-(2-trimethylammonioethyl) phosphate and (3-octadecanesulphonyl-2-methoxymethyl-propyl)-(2-trimethylammonioethyl) phosphate.

The present invention also includes all stereoisomeric compounds of general formula I which arise, for example, due to the asymmetric carbon atom or the sulphoxide group.

DETAILED DESCRIPTION OF THE INVENTION

Figure 1:
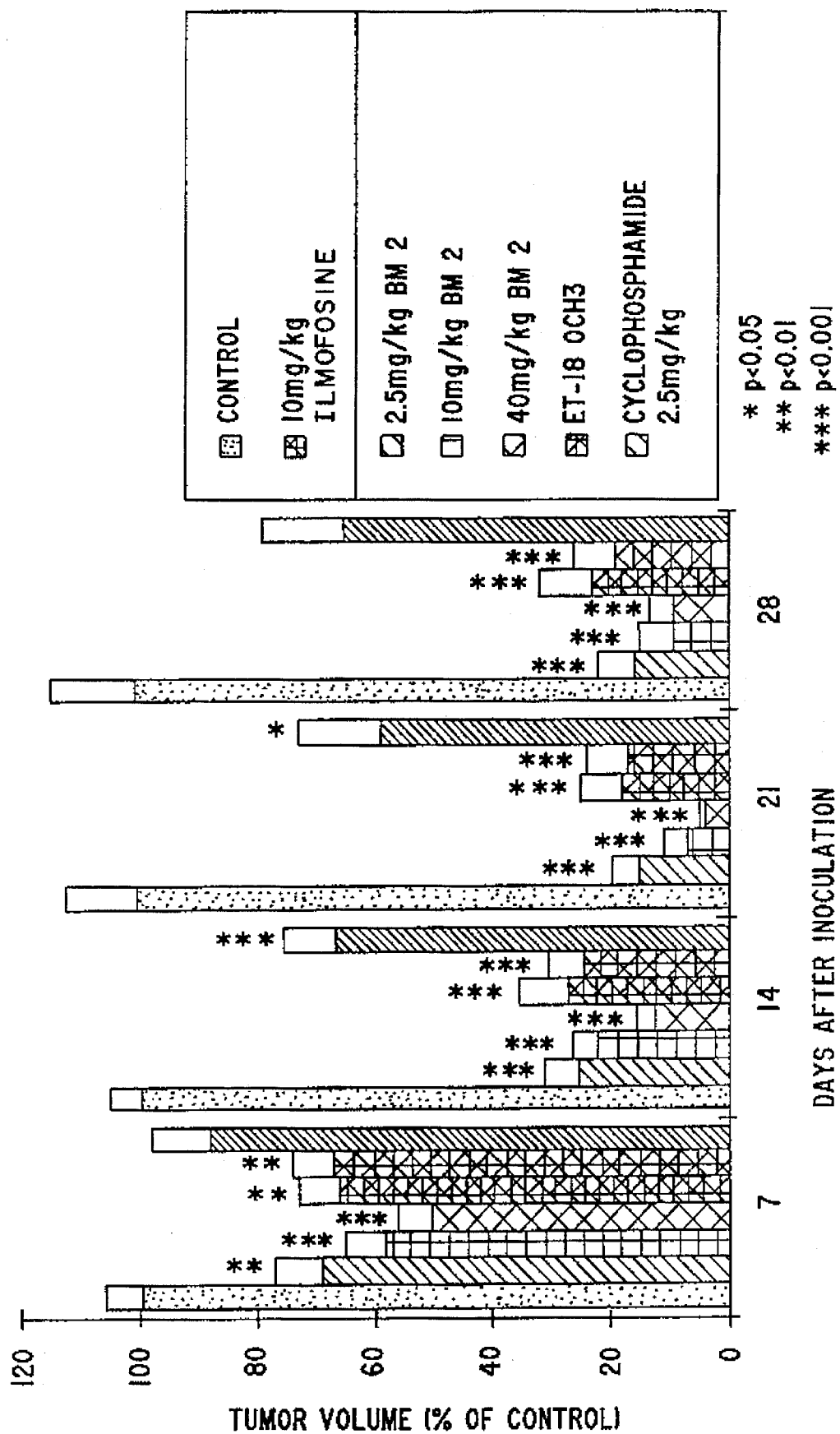
FIG. 1 is a bar graph illustrating the percentage decrease in tumor volume (with reference to an untreated control) plotted against days after mice were inoculated with meth-A tumor cells and treated with known compounds and compounds according to the present invention.

The compounds of general formula I can be prepared in known manner, for example

I) by treating a compound of the general formula II, which can also be present as a racemate or as an enantiomer:

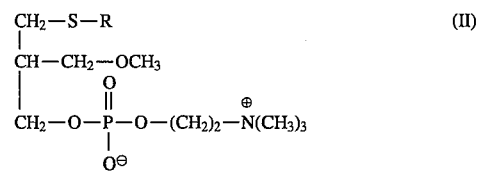

in which R has the above-given meaning, with an oxidizing agent, or

II) by reacting a compound of the general formula III, which can be present as a racemate or as an enantiomer:

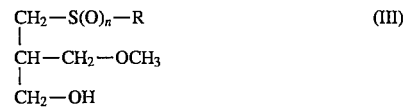

in which n and R have the above-given meanings, a) with a compound of the general formula:

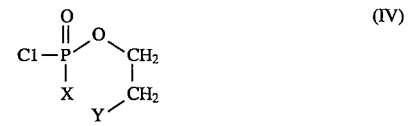

in which x is a chlorine atom and Y is a bromine atom or X and y together represent an oxygen atom, in the presence of an acid-binding agent and treating the reaction product with trimethylamine, whereby, when X is a chlorine atom, a selective hydrolysis precedes the amination, or b) by converting into a compound of the general formula:

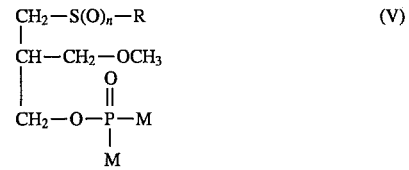

in which n and R have the above-given meanings and M is a hydroxyl group, a chlorine or bromine atom or an alkylthio radical and reacting this with a compound of the general formula:

in which T is a chlorine or bromine atom or an —$N(CH_3)_3^+$ $Hal^-$ radical, in which $Hal^-$ is a chloride, bromide or iodide ion, and, when T is a chlorine or bromine atom, the intermediate product thus obtained is quaternized with trimethylamine, or c) by reacting with a compound of the general formula:

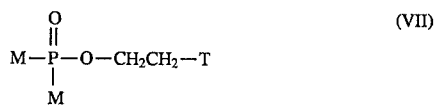

in which M and T have the above-given meanings, in the presence of an acid- or water-forming agent and optionally converting into an internal salt.

In the cases of process I, 30% hydrogen peroxide in glacial acetic acid is preferably used as the oxidation agent. In the case of the use of equimolar amounts, sulphoxides are obtained and, with a three to five fold excess of oxidizing agent, there are obtained the corresponding sulphones. However, for the oxidation, there can also very well be used an organic peroxide, for example m-chloroperbenzoic acid, in which case in inert solvent is used, for example methylene chloride. The reaction temperature is from 0° to 50° C. and preferably 20° C.

The thioethers of general formula II used as starting compounds are described in U.S. Pat. No. 4,444,766, the disclosure of which is incorporated herein by reference, or can be prepared according to the methods described therein.

The methods given in the case of process II are also described in U.S. Pat. No. 4,444,766. The sulphoxides or sulphones of the general formula III thereby used can be obtained analogously to the oxidation described in process I from the corresponding thioethers, which are also described in U.S. Pat. No. 4,444,766 or can be prepared according to the methods described therein.

The optically active intermediates stages of the general formula III needed for the synthesis of the enantiomer-pure compounds can be prepared, for example, by the following method. An alcohol of general formula III present as a racemate is converted, with the help of an optically active auxiliary reagent, into a diastereomer pair, this is separated with the help of column-chromatographic methods and the enantiomer-pure alcohol of general formula III is obtained herefrom, in each case, by splitting off the auxiliary reagent. Thus, as auxiliary reagent, an optically active acid, for example (R)- or (S)-2-phenylpropionic acid or (S)-camphanic acid, can be esterified with an alcohol of general formula III. After separation of the diastereomers, the esters are saponified under acidic but preferably alkaline conditions. The same process can also be used for the separation of the thioether alcohols which are used as precursors for the synthesis of compounds of general formula III. These so separated thioether alcohols can then be reacted analogously to the methods described in process II to give optically active compounds of general formula II which can be used as starting material for process I.

The pharmacologically acceptable salts are obtained in the usual way, for example by neutralization of the compounds of general formula I with non-toxic inorganic or organic acids, for example hydrochloric acid, sulfuric acid, phosphoric acid, hydrobromic acid, acetic acid, lactic acid, citric acid, malic acid, salicylic acid, malonic acid, maleic acid or succinic acid.

The new compounds of general formula I according to the present invention and the salts thereof can be administered enterally or parenterally in liquid or solid form. There can be used all conventional forms of administration, for example tablets, capsules, dragees, syrups, solutions, suspensions and the like. As injection medium, water is preferably used which contains the additives usual in the case of injection solutions, such as stabilizing agents, solubilizing agents and/or buffers.

Such additives include, for example, tartrate and citrate buffers, ethanol, complex formers (such as ethylenediaminetetraacetic acid and the non-toxic salts thereof) and high molecular weight polymers (such as liquid polyethylene oxide) for viscosity regulation. Liquid carrier materials for injection solutions must be sterile and are preferably filled into ampoules. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening agents.

The dosage can depend upon various factors, such as the mode of administration, species, age and/or individual state. The doses to be administered daily are from about 0.05 to 100 mg./kg. body weight.

The action of the compounds was tested in an in vivo model on methylcholanthrene-induced fibrosarcoma of the mouse.

Experimental Description

Female $CB_6F_1$ mice were injected i.c. on day 0 with $1 \times 10^5$ meth-A cells. The therapy took place daily from day 1 up to day 21 with 2.5, 10 and 40 mg./kg. p.o. Number of animals per group: 10. As parameters, there were determined:

1) the tumor volume on day 7, 14, 21 and 28 after tumor cell inoculation.

2) the tumor weight on day 28.

Figure 2:
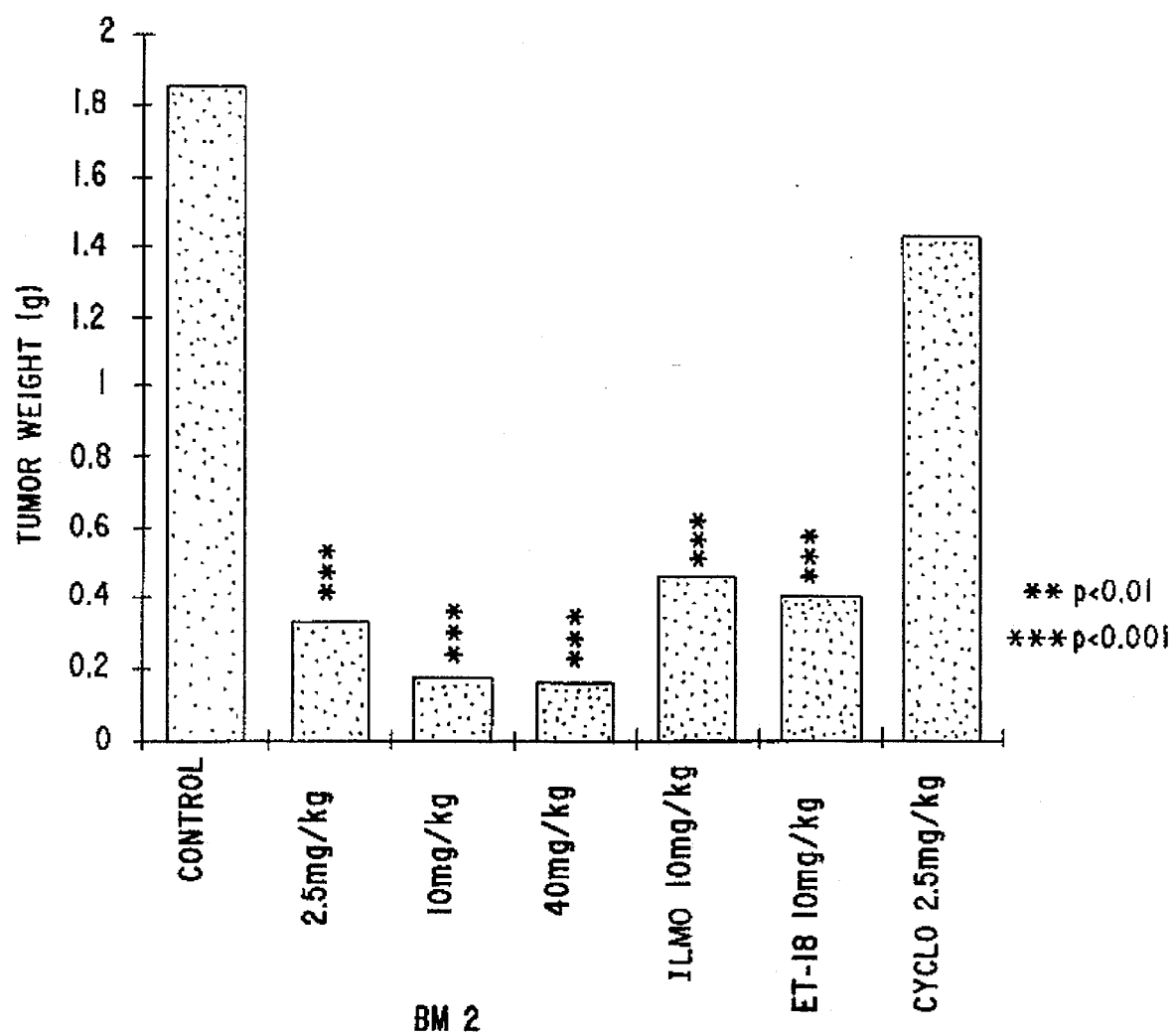
FIG. 2 is a bar graph illustrating the weight of the tumors in the mice treated as described in FIG. 1 28 days after inoculation.

As comparative substances, there were used the compound which was not oxidized on the sulphur atom (3-hexa-decylthio-2-methoxymethylpropyl)-(2-trimethyl-ammonioethyl) phosphate (ilmofosine), known from U.S. Pat. No. 4,444,766, and the compound (3-octadecyloxy-2-methoxypropyl)-(2-trimethyl-ammonioethyl) phosphate (ET-18-$OCH_3$), and, as positive control, cyclophosphamide was also used (see FIGS. 1 and 2 of the accompanying drawings in which in FIG. 1 the tumor volume, expressed as a percentage of the control, is plotted against the number of days after tumor cell inoculation and in FIG. 2 are shown the tumor weights at day 28 after tumor cell inoculation).

In the case of the consideration of the tumor volume, it can clearly be seen that 2.5 mg. (3-hexa-decanesulphonyl-2-methoxymethylpropyl)-(2-trimethyl-ammonioethyl) phosphate (BM 2) shows the same effectiveness as 10 mg. ilmofosine. The tumor weight on day 28 shows the same result. Thus BM 2 is clearly more effective than ilmofosine.

The following Examples are given for the purpose of illustrating the present invention:

EXAMPLE 1

(3-Hexadecanesulphonyl-2-methoxymethylpropyl)-(2-trimethylammonioethyl) phosphate To 7.56 g. (14 mole) (3-hexadecylthio-2-methoxymethylpropyl)-(2-trimethylammonioethyl) phosphate in 70 ml. glacial acetic acid are added 4.2 ml. (42 mole) 30% hydrogen peroxide and the reaction mixture stirred at ambient temperature. After 24 hours, 1.4 ml. hydrogen peroxide are again added thereto and stirring continued for a total of 72 hours. The solution is evaporated on a rotary evaporator at 20° C. and the residue is mixed with diethyl ether and left to stand overnight in a refrigerator. The ethereal solution is decanted off from the viscous residue which is dissolved in 1 liter of water and the solution freeze-dried. There are thus obtained 5.2 g. (65% of theory) of the desired compound in amorphous form containing 1 mole of water; $R_f$ value on an RP-18 silica gel plate with the elution agent mixture acetone/water (7:3 v/v)+0.1% glacial acetic acid: 0.35; SO derivative: 0.39; starting material: 0.28.

The following sulphonyl derivatives are prepared in an analogous way by using the (−) or (+) enantiomeric thioethers:

a) (−)-(3-hexadecanesulphonyl-2-methoxymethylpropyl)-(2-trimethylammonioethyl) phosphate
b) (+)-(3-hexadecanesulphonyl-2-methoxymethylpropyl)-(2-trimethylammonioethyl) phosphate
c) (3-octadecanesulphonyl-2-methoxymethylpropyl)-(2-trimethylammonioethyl) phosphate
d) (−)-(3-octadecanesulphonyl-2-methoxymethylpropyl)-(2-trimethylammonioethyl) phosphate
e) (+)-(3-octadecanesulphonyl-2-methoxymethylpropyl)-(2-trimethylammonioethyl) phosphate

EXAMPLE 2

(3-Hexadecanesulphinyl-2-methoxymethylpropyl)-(2-trimethylammonioethyl) phosphate To 10.8 g. (20 mmole) (3-hexadecylthio-2-methoxymethylpropyl)-(2-trimethylammonioethyl) phosphate in 100 ml. glacial acetic acid are added 2 ml. (20 mmole) 30% hydrogen peroxide and the solution is left to stand for 144 hours at ambient temperature. The solution is evaporated on a rotary evaporator and the residue is, in each case, taken up twice in toluene and again evaporated. Subsequently, the residue is stirred with 250 ml. acetone, a small amount of insoluble material is filtered off and the filtrate is allowed to evaporate slowly. After about half of the acetone has evaporated, a precipitate is obtained. This is filtered off with suction to give 3.0 g. (27% of theory) of the desired product, m.p. 235°–240° C.; $R_f$ value on an RP-18 silica gel plate with the elution agent mixture acetone/water (7:3 v/v)+0.1% glacial acetic acid: 039; $SO_2$ derivative: 0.35; starting material: 0.28.

The following sulphoxides are prepared in analogous way by use of the (−) or (+) enantiomeric thioether:

a) (−)-(3-hexadecanesulphinyl-2-methoxymethylpropyl)-(2-trimethylammonioethyl) phosphate
b) (+)-(3-hexadecanesulphinyl-2-methoxymethylpropyl)-(2-trimethylammonioethyl) phosphate.

EXAMPLE 3

Analogously to Example 2, by the use of the corresponding octadecyl derivative, there is prepared (3-octadecanesulphinyl-2-methoxymethylpropyl)-(2-trimethylammonioethyl) phosphate, and by use of the corresponding (−) or (+) enantiomeric thioethers a) (−)-(3-octadecanesulphinyl-2-methoxymethylpropyl)-(2-trimethylammonioethyl) phosphate, and
b) (+)-(3-octadecanesulphinyl-2-methoxymethylpropyl)-(2-trimethylammonioethyl) phosphate are prepared.

What is claimed is:

1. A compound of the formula

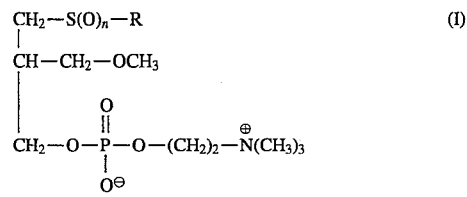

in which n is 1 or 2 and R is a straight-chained, saturated alkyl group containing 16 to 18 carbon atoms, steroisomers thereof, and pharmacologically acceptable salts thereof.

2. A compound according to claim 1 wherein n is 1.

3. A compound according to claim 2 wherein R contains 16 carbon atoms.

4. A compound according to claim 2 wherein R contains 18 carbon atoms.

5. A compound according to claim 1 selected from the group consisting of (3-hexadecylsulphinyl-2-methoxy-methylpropyl)-(2-trimethylammonioethyl) phosphate, (3-octadecylsulphinyl-2-methoxymethylproply)-(2-trimethylammonioethyl) phosphate and the (+) and (−) entantiomers thereof.

6. A compound according to claim 1 wherein n is 2.

7. A compound according to claim 6 wherein R contains 16 carbon atoms.

8. A compound according to claim 6 wherein R contains 18 carbon atoms.

9. A compound according to claim 1 selected from the group consisting of (3-hexadecylsulphonyl-2-methoxy-methylpropyl)-(2-trimethylammonioethyl) phosphate, (3-octadecylsulphonyl-2-methoxymethylproply)-(2-trimethylammonioethyl) phosphate and the (+) and (−) entantiomers thereof.

10. A pharmaceutical composition comprising a compound of claim 1 and a pharmaceutically acceptable carrier.

11. A pharmaceutical composition according to claim 10 wherein the compound is (3-hexadecanesulphonyl-2-methoxymethylpropyl)-(2-trimethylammonioethyl) phosphate.

12. A pharmaceutical composition according to claim 10 wherein the compound is (3-octadecanesulphonyl-2-methoxymethylpropyl)-(2-trimethylammonioethyl) phosphate.

* * * * *